United States Patent
Seebach et al.

(10) Patent No.: US 7,015,185 B2
(45) Date of Patent: Mar. 21, 2006

(54) AMMONIUM NITRILES AND THE USE THEREOF AS HYDROPHOBIC BLEACHING ACTIVATORS

(75) Inventors: Michael Seebach, Hofheim (DE); Gerd Reinhardt, Kelkheim (DE)

(73) Assignee: Clariant GmbH, Frankfurt (DE)

( * ) Notice: Subject to any disclaimer, the term of this patent is extended or adjusted under 35 U.S.C. 154(b) by 16 days.

(21) Appl. No.: 10/486,939

(22) PCT Filed: Mar. 12, 2003

(86) PCT No.: PCT/EP03/02543

§ 371 (c)(1),
(2), (4) Date: Jul. 26, 2004

(87) PCT Pub. No.: WO03/078561

PCT Pub. Date: Sep. 25, 2003

(65) Prior Publication Data

US 2004/0266644 A1 Dec. 30, 2004

(30) Foreign Application Priority Data

Mar. 15, 2002 (DE) ................ 102 11 389

(51) Int. Cl.
*C11D 1/00* (2006.01)
*C11D 3/26* (2006.01)
*C11D 3/395* (2006.01)

(52) U.S. Cl. ............ 510/220; 510/221; 510/224; 510/314; 510/504; 252/186.27; 558/303

(58) Field of Classification Search .......... 510/220, 510/221, 224, 314, 504; 252/186.25; 422/28; 558/303, 388, 430, 435
See application file for complete search history.

(56) References Cited

U.S. PATENT DOCUMENTS

| 4,144,226 | A | 3/1979 | Crutchfield et al. |
|---|---|---|---|
| 4,146,495 | A | 3/1979 | Crutchfield et al. |
| 4,751,015 | A | 6/1988 | Humphreys et al. |
| 4,915,863 | A | 4/1990 | Aoyagi et al. |
| 4,933,103 | A | 6/1990 | Aoyagi et al. |
| 5,236,616 | A | 8/1993 | Oakes et al. |
| 5,281,361 | A | 1/1994 | Adams et al. |
| 5,616,550 | A | 4/1997 | Kruse et al. |
| 5,856,165 | A | 1/1999 | van Solingen |
| 6,225,274 | B1 * | 5/2001 | Nitsch et al. ........... 510/314 |
| 6,313,081 | B1 | 11/2001 | Lenting et al. |
| 6,407,045 | B1 * | 6/2002 | Nitsch et al. ........... 510/220 |
| 6,767,879 | B1 | 7/2004 | Lenting et al. |

FOREIGN PATENT DOCUMENTS

| CA | 2299437 | * | 8/2000 |
|---|---|---|---|
| EP | 790244 | | 8/1997 |
| EP | 1122300 | * | 8/2001 |
| GB | 1 382 594 | | 2/1975 |
| WO | WO 92/11347 | | 7/1992 |
| WO | WO 94/23005 | | 1/1996 |

OTHER PUBLICATIONS

David Luten, Jr., "The Preparation of Aminonitriles and their Quatenary Ammonium Derivatives", Journal of Organic Chemistry, No. 3, 1938, pp 588-597.
Abstract for EP 790, Aug. 20, 1997.
Abstract for WO 92/11347, Jul. 9, 1992.
Abstract for WO 96/34092, Jul. 27, 2004.

* cited by examiner

*Primary Examiner*—Gregory R. Del Cotto
(74) *Attorney, Agent, or Firm*—Richard P. Silverman

(57) ABSTRACT

The invention relates to ammonium nitriles of general formula (I), wherein the radicals $R^3$, $R^4$, $R^5$ and $X^-$ have the meaning as cited in the description and $R^1$ and $R^2$ respectively represent individually a straight or branched chained $C_5$–$C_{24}$-alkyl, alkenyl or alkylether group. The inventive compounds are used as bleaching activators in washing, cleaning, and disinfective agents and in textile and paper bleaching.

7 Claims, No Drawings

AMMONIUM NITRILES AND THE USE THEREOF AS HYDROPHOBIC BLEACHING ACTIVATORS

This invention relates to ammonium nitriles and to the use thereof for intensifying the bleaching effect of peroxygen compounds during the bleaching of colored soilings both on textiles and also on hard surfaces, and to washing and cleaning compositions which comprise these nitriles as bleaching activators.

Inorganic peroxygen compounds, in particular hydrogen peroxide and solid peroxygen compounds which dissolve in water with the release of hydrogen peroxide, such as sodium perborate and sodium carbonate perhydrate, have been used for a long time as oxidizing agents for disinfection and bleaching purposes. The oxidizing effect of these substances greatly depends, in dilute solutions, on the temperature; thus, for example, using hydrogen peroxide or perborate in alkaline bleaching liquors, an adequately rapid bleaching of soiled textiles is achieved only at temperatures above about 80° C.

It is known that the oxidizing effect of peroxidic bleaching agents, such as perborates, percarbonates, persilicates and perphosphates at low temperatures can be improved by adding precursors of bleaching peroxy acids, so-called bleaching activators. Many substances are known as bleaching activators according to the prior art. These are usually reactive organic compounds with an O-acyl or N-acyl group which, in alkaline solution together with a source of hydrogen peroxide, form the corresponding peroxy acids.

Representative examples of bleaching activators are N,N,N',N'-tetraacetylethylenediamine (TAED), glucose pentaacetate (GPA), xylose tetraacetate (TAX), sodium 4-benzoyloxybenzenesulfonate (SBOBS), sodium trimethylhexanoyloxybenzenesulfonate (STHOBS), tetraacetylglycoluril (TAGU), tetraacetylcyanic acid (TACA), di-N-acetyldimethylglyoxime (ADMG), 1-phenyl-3-acetylhydantoin (PAH), sodium nonanoyloxybenzenesulfonate (NOBS) and sodium isononanoyloxybenzenesulfonate (ISONOBS).

As a result of the addition of these substances the bleaching effect of aqueous peroxide solutions can be increased so much that essentially the same effects arise at temperatures around 60° C. as with peroxide solution on its own at 95° C.

In the meantime some cationic compounds which contain a quaternary ammonium group have gained in importance since they represent highly effective bleaching activators. Such cationic bleaching activators are described, for example, in GB-A-1 382 594, U.S. Pat. No. 4,751,015, EP-A-0 284 292, EP-A-0 331 229.

Ammonium nitrites of the formula

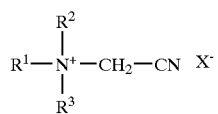

form a particular class of cationic bleaching activators. Compounds of this type and the use thereof as activators in bleaching compositions are described in EP-A-303 520, EP-A-458 396 and EP-A-464 880. In the compounds described therein, the nitrogen atom of the ammonium group is substituted by alkyl, alkenyl or aryl groups, where at most one of the substituents has a chain length greater than C4.

Ammonium nitrites of this type, where two of the groups $R^1$, $R^2$ or $R^3$ represent a long-chain alkyl group, are covered by the formula in WO 98/23719 and WO 00/36061, but have not already been described expressly therein.

Presumably, during the perhydrolysis, these compounds form a peroxyimidic acid which acts as a bleaching agent.

The described compounds develop their bleaching effect primarily on hydrophilic soilings such as tea or red wine, whereas their effectiveness on hydrophobic soilings, such as curry or ketchup stains, is significantly reduced.

Surprisingly, it has now been found that ammonium nitriles of the type described above, which have at least two alkyl, alkenyl or alkyl ether substituents with a chain length greater than C4 develop a better bleaching effect on hydrophobic soilings than the nitriles according to the prior art.

The present invention thus provides compounds of the formula

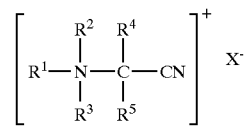

in which $R^1$ and $R^2$ are in each case individually a straight-chain or branched-chain $C_5$- to $C_{24}$-alkyl, alkenyl or alkyl ether group, preferably a $C_5$- to $C_{18}$-alkyl, alkenyl or alkyl ether group, $R^3$ is $C_1$- to $C_{24}$-alkyl, $C_2$- to $C_{24}$-alkenyl, cyanomethyl or $C_1$–$C_4$-alkoxy-$C_1$- to $C_4$-alkyl, preferably $C_1$- to $C_8$-alkyl, $C_2$- to $C_8$-alkenyl or $C_1$-alkoxy-$C_1$- to $C_4$-alkyl, $R^4$ and $R^5$ are hydrogen, $C_1$- to $C_4$-alkyl, $C_2$- to $C_4$-alkenyl, $C_1$–$C_4$-alkoxy-$C_1$–$C_4$-alkyl, phenyl, $C_1$- to $C_3$-alkylphenyl, or together with the common carbon atom form a $C_5$- to $C_7$-cycloalkyl group, preferably hydrogen, methyl or phenyl, where in particular $R_4$ is hydrogen if $R_5$ is not hydrogen, and $X^-$ is an anion, for example chloride, bromide, iodide, fluoride, sulfate, hydrogensulfate, carbonate, hydrogencarbonate, phosphate, mono- and dihydrogenphosphate, pyrophosphate, metaphosphate, nitrate, methosulfate, dodecylsulfate, dodecylbenzenesulfonate, phosphonate, methylphosphonate, methanedisulfonate, methylsulfonate, ethanesulfonate, toluenesulfonate, benzenesulfonate or cumenesulfonate.

Particular preference is given to those cationic nitriles in which $R^1$ and $R^2$ is $C_6$- to $C_{10}$-alkyl,
$R^3$ is $C_1$- to $C_6$-alkyl,
$R^4$ and $R^5$ are hydrogen and
$X^-$ is, chloride, hydrogensulfate, sulfate, methosulfate, toluenesulfonate, benzenesulfonate or cumenesulfonate.

Examples of these particularly preferred cationic nitriles are (cyanomethyl)-di-n-hexylmethylammonium tosylate, (cyanomethyl)methyl-di-n-octylammonium chloride, (cyanomethyl)ethyl-di-n-hexylammonium methosulfate, (cyanomethyl)-di-n-decylmethylammonium hydrogensulfate, (cyanomethyl)-di-n-hexylmethylammonium benzenesulfonate or (cyanomethyl)-di-n-octylmethylammonium-cumenesulfonate.

By referring to a number of general examples, the aim is to illustrate the synthetic routes for the cationic nitriles of this invention:

1. The secondary amine of the formula $NHR^1R^2$ is initially introduced together with a base, preferably alkali metal carbonate or alkali metal hydroxide, in a solvent, preferably in absolute ethanol or in a toluene/water mixture. At temperatures between 0 and 50° C., preferably at 10 to 30° C., chloroacetonitrile is added dropwise. After a reaction time of 1 to 50 hours, the organic phase is separated off and the aqueous phase is extracted with an organic solvent. The solvent is stripped off from the combined organic phases. The resulting crude product can be further purified by fractional distillation. The resulting dialkylaminoacetonitrile is taken up in an organic solvent and reacted with an alkylating agent, such as methyl chloride, dimethyl sulfate or arylsulfonic acid alkyl ester, at temperatures between 20 and 100° C. to give the corresponding N-cyanomethylammonium salt. The salt can be obtained by conventional work-up methods, such as extraction, crystallization, suction filtration, washing of the crystal slurry on the suction filter and drying.

2. Tertiary amine and chloroacetonitrile are reacted in a suitable solvent, e.g. in acetone, for 1 to 12 hours at temperatures between 10 and 70° C. The resulting precipitate, the N-cyanomethylammonium chloride is filtered off, washed with an organic solvent and dried.

3. Secondary amine, sodium cyanide and an aldehyde or a ketone, preferably formaldehyde in the form of a 36% strength formalin solution, are combined in a solvent, preferably an ethanol/water mixture or water. After a reaction time of 1 to 12 hours at temperatures between 10 and 80° C., preferably at 10 to 30° C., aqueous hydrochloric acid is added to the mixture. The aqueous phase is extracted with a suitable organic solvent, e.g. methylene chloride or diethyl ether. The combined organic phases are dried over magnesium sulfate and the solvent is stripped off. The resulting crude product can be further purified by fractional distillation. The resulting dialkylaminoacetonitrile is taken up in an organic solvent and reacted with an alkylating agent, such as methyl chloride, dimethyl sulfate or arylsulfonic alkyl ester, at temperatures between 20 and 100° C. to give the corresponding N-cyanomethylammonium salt. The salt can be obtained by customary work-up methods, such as extraction, crystallization, suction filtration, washing of the crystal slurry on the suction filter and drying.

The invention also provides for the use of these ammonium nitrites as bleaching activators in bleaching washing and cleaning compositions.

The term "bleaching" here is understood as meaning both the bleaching of soiling on the textile surface, and also the bleaching of soiling released from the textile surface in the wash liquor. For the bleaching of stains on hard surfaces, the same applies analogously. Further potential applications are in the personal care sector, e.g. for the bleaching of hair and for improving the effectiveness of denture cleaners. In addition, the complexes according to the invention are used in commercial laundries, in the bleaching of wood and paper, the bleaching of cotton and in disinfectants.

The invention further relates to a method of cleaning textiles, such as hard surfaces, in particular of dishes, using said cationic nitriles in an aqueous solution which optionally comprises further washing or cleaning composition constituents, in particular oxidizing agents based on peroxygen, and washing compositions and cleaning compositions for hard surfaces, in particular dishwashing compositions, preference being given to those for use in machine processes, which comprise cationic nitriles of this type.

The use according to the invention consists essentially in creating, in the presence of a hard surface contaminated with colored soilings or a correspondingly soiled textile, conditions under which a peroxidic oxidizing agent and the cationic nitrile can react together with the aim of obtaining secondary products with a stronger oxidizing effect. Such conditions are present particularly when the reactants meet one another in aqueous solution. This can occur as a result of the separate addition of the peroxygen compound and of a cationic nitrile to a solution which optionally contains washing or cleaning composition. However, the process according to the invention is particularly advantageously carried out using an inventive washing composition or cleaning composition for hard surfaces which comprises the cationic nitriles and optionally a peroxygen-containing oxidizing agent. The peroxygen compound can also be added to the solution separately without a diluent or in the form of a preferably aqueous solution or suspension if a peroxygen-free washing or cleaning composition is used.

The washing and cleaning compositions according to the invention, which may be present in the form of granules, pulverulent or tablet-shaped solids, other shaped bodies, homogenous solutions or suspensions, can in principle comprise all ingredients which are known and customary in such compositions apart from said bleach-enhancing active ingredient. The compositions according to the invention can, in particular, comprise builder substances, surface-active surfactants, peroxygen compounds, additional peroxygen activators or organic peracids, water-miscible organic solvents, sequestering agents, thickeners, preservatives, perlizing agents, emulsifiers and enzymes, and special additives with color- or fiber-care effect. Further auxiliaries such as electrolytes, pH regulators, silver corrosion inhibitors, foam regulators, and dyes and fragrances are possible.

A cleaning composition for hard surfaces according to the invention can, moreover, comprise constituents with an abrasive action, in particular from the group comprising quartz flours, wood flours, plastic flours, chalks and microglass spheres, and mixtures thereof. Abrasive substances are present in the cleaning compositions according to the invention preferably not exceeding 20% by weight, in particular from 5 to 15% by weight.

Suitable peroxidic bleaches are hydrogen peroxide and compounds which release hydrogen peroxide under the washing and cleaning conditions, such as alkali metal peroxides, organic peroxides, such as urea-hydrogen peroxide adducts and inorganic persalts, such as alkali metal perborates, percarbonates, perphosphates, persilicates, persulfates and peroxynitrites. Mixtures of two or more of these compounds are likewise suitable. Particular preference is given to sodium perborate tetrahydrate and, in particular, sodium perborate monohydrate, and sodium percarbonate. Sodium perborate monohydrate is preferred because of its good storage stability and its good solubility in water. Sodium percarbonate may be preferred for ecological reasons.

Alkali metal hydroperoxides are a further suitable group of peroxide compounds. Examples of these substances are cumene hydroperoxide and t-butyl hydroperoxide.

Aliphatic or aromatic mono- or dipercarboxylic acids, and the corresponding salts are also suitable peroxy compounds. Examples thereof are peroxynaphthoic acid, peroxylauric acid, peroxystearic acid, N,N-phthaloylaminoperoxycaproic acid, 1,12-diperoxydodecanedioic acid, 1,9-diperoxyazelaic acid, diperoxysebacic acid, diperoxyisophthalic acid, 2-decyldiperoxybutane-1,4-dioic acid and 4,4'-sulfonylbisperoxybenzoic acid.

In such washing and cleaning compositions, the cationic, nitrilic bleaching activator according to the invention may be present in a weight fraction of from about 0.1 to 20%, preferably from 0.5 to 10%, in particular from 0.5 to 5.0% together with a peroxy compound. The weight content of this peroxy compound is usually from 2 to 40%, preferably from 4 to 30%, in particular from 10 to 25%.

In addition to the cationic, nitrilic bleaching activators according to the invention, other suitable bleaching activators may also be present in the washing and cleaning compositions in the customary amounts (about 1 to 10% by weight). Suitable bleaching activators are organic compounds with an O-acyl or N-acyl group, in particular from the group of activated carboxylic esters, in particular sodium nonanoyloxybenzenesulfonate, sodium isononanoyloxybenzenesulfonate, sodium 4-benzoyloxybenzenesulfonate, sodium trimethylhexanoyloxybenzenesulfonate, carboxylic anhydrides, in particular phthalic anhydride, acylated polyhydric alcohols, in particular triacetin, ethylene glycol diacetate, 2,5-diacetoxy-2,5-dihydrofuran, lactones, acylals, carboxamides, acyllactams, acylated ureas and oxamides, N-acylated hydantoins, for example 1-phenyl-3-acetylhydantoin, hydrazides, triazoles, hydrotriazines, urazoles, diketopiperazides, sulfurylamides, polyacylated alkylenediamines, for example N,N,N',N'-tetraacetylethylenediamine, acylated triazine derivatives, in particular 1,5-diacetyl-2,4-dioxohexahydro-1,3,5-triazine, acylated glycolurils, in particular tetraacetylglycoluril, N-acylimides, in particular N-nonaoylsuccinimide, and acylated sugar derivatives, in particular pentaacetylglucose (PAG), pentaacetylfructose, tetraacetylxylose and octaacetyllactose, and acetylated, optionally N-alkylated glucamine and gluconolactone and/or N-acylated lactams, for example N-benzoylcaprolactam, but also quaternary nitrile compounds, for example quaternary trialkylammoniumnitrile salts, as are described in EP-A-303 520, EP-A-458 396 and EP-A-464 880, in particular the cyanomethyltrimethylammonium salts, but also heterocyclically substituted quaternary nitrile compounds, as described in EP-A-790 244.

In addition to the conventional bleaching activators listed above, or instead of them, it is also possible for sulfonimines, open-chain or cyclic quaternary iminium compounds, such as dihydroisoquinoliniumbetains and/or further bleach-enhancing transition metal salts or mono- or polynuclear transition metal complexes with acyclic or macrocyclic ligands to be present.

The washing and cleaning compositions may comprise one or more surfactants, where, in particular, anionic surfactants, nonionic surfactants and mixtures thereof, but also cationic, zwitterionic and amphoteric surfactants are suitable. Such surfactants are present in washing compositions according to the invention in quantitative amounts of from preferably 1 to 50% by weight, in particular from 3 to 30% by weight, whereas in cleaning compositions for hard surfaces normally lower contents, i.e. amounts up to 20% by weight, in particular up to 10% by weight and preferably in the range from 0.5 to 5% by weight, are present. In cleaning compositions for use in machine dishwashing processes, low-foam compounds are normally used.

Suitable anionic surfactants are, in particular, soaps and those which contain sulfate or sulfonate groups. Suitable surfactants of the sulfonate type are preferably $C_9$–$C_{13}$-alkylbenzenesulfonates, olefin sulfonates, i.e. mixtures of alkene- and hydroxyalkanesulfonates, and disulfonates, as are obtained for example from monoolefins with a terminal or internal double bond by sulfonation with gaseous sulfur trioxide and subsequent alkaline or acidic hydrolysis of the sulfonation products. Also suitable are alkanesulfonates, which are obtained from $C_{12}$–$C_{18}$-alkanes, for example by sulfochlorination or sulfoxidation with subsequent hydrolysis or neutralization. Also suitable are the esters of alpha-sulfo fatty acids (estersulfonates), for example the alpha-sulfonated methyl esters of hydrogenated coconut, palm kernel or tallow fatty acids, which are prepared by sulfonation of the methyl esters of fatty acids of vegetable and/or animal origin having 8 to 20 carbon atoms in the fatty acid molecule and subsequent neutralization to give water-soluble monosalts.

Further suitable anionic surfactants are sulfated fatty acid glycerol esters, which represent mono-, di- and triesters, and mixtures thereof. As alk(en)ylsulfates, preference is given to the alkali metal and, in particular, the sodium salts of sulfuric half-esters of $C_{12}$–$C_{18}$-fatty alcohols, for example of coconut fatty alcohol, tallow fatty alcohol, lauryl, myristyl, cetyl or stearyl alcohol or of $C_8$–$C_{20}$-oxo alcohols and those half-esters of secondary alcohols of this chain length. Also preferred are alk(en)ylsulfates of said chain length which contain a synthetic straight-chain alkyl radical prepared on a petrochemical basis. 2,3-Alkylsulfates are also suitable anionic surfactants. Also suitable are the sulfuric monoesters of the straight-chain or branched alcohols ethoxylated with 1 to 6 mol of ethylene oxide, such as 2-methyl-branched $C_9$–$C_{11}$-alcohols having on average 3.5 mol of ethylene oxide (EO) or $C_{12}$–$C_{18}$-fatty alcohols with 1 to 4 EO.

Preferred anionic surfactants also include the salts of alkylsulfosuccinic acid, which are also referred to as sulfosuccinates or isosulfosuccinic esters, and which represent monoesters and/or diesters of sulfosuccinic acid with alcohols, preferably fatty alcohols and, in particular, ethoxylated fatty alcohols. Preferred sulfosuccinates contain $C_8$–$C_{18}$-fatty alcohol radicals or mixtures of these. Suitable further anionic surfactants are fatty acid derivatives of amino acids, for example of N-methyltaurine (taurides) and/or of N-methylglycine (sarcosinates). Suitable further anionic surfactants are, in particular, soaps, for example in amounts of from 0.2 to 5% by weight. Saturated fatty acid soaps, such as the salts of lauric acid, myristic acid, palmitic acid, stearic acid, hydrogenated erucic acid and behenic acid, and, in particular, soap mixtures derived from natural fatty acids, e.g. coconut, palm kernel or tallow fatty acids, are particularly suitable.

The anionic surfactants, including the soaps, can be present in the form of their sodium, potassium or ammonium salts and in the form of soluble salts of organic bases, such as mono-, di- or triethanolamine. The anionic surfactants are preferably in the form of their sodium or potassium salts, in particular in the form of sodium salts. Anionic surfactants are present in the washing compositions according to the invention preferably in amounts of from 0.5 to 10% by weight and in particular in amounts of from 5 to 25% by weight.

The nonionic surfactants used are preferably alkoxylated, advantageously ethoxylated, in particular primary alcohols having preferably 8 to 18 carbon atoms and on average 1 to 12 mol of ethylene oxide (EO) per mole of alcohol, in which the alcohol radical may be linear or methyl-branched preferably in the 2 position, or can contain linear and methyl-branched radicals in the mixture, as are usually present in oxoalcohol radicals.

However, particular preference is given to alcohol ethoxylates with linear radicals from alcohols of natural origin having 12 to 18 carbon atoms, e.g. from coconut, palm, tallow fatty or oleyl alcohol, and on average 2 to 8 EO per mole of alcohol. Preferred ethoxylated alcohols include, for example, $C_{12}$–$C_{14}$-alcohols with 3 EO or 4 EO, $C_9$–$C_{11}$-alcohols with 7 EO, $C_{13}$–$C_{15}$-alcohols with 3 EO, 5 EO, 7 EO or 8 EO, $C_{12}$–$C_{18}$-alcohols with 3 EO, 5 EO or 7 EO and mixtures thereof, such as mixtures of $C_{12}$–$C_{14}$-alcohol with 3 EO and $C_{12}$–$C_{18}$-alcohol with 7 EO. The given degree of ethoxylation are statistical average values which may be an integer or a fraction for a specific product.

Preferred alcohol ethoxylates have a narrowed homolog distribution (narrow range ethoxylates, NRE). In addition to these nonionic surfactants, fatty alcohols with more than 12 EO can also be used. Examples thereof are (tallow) fatty alcohols with 14 EO, 16 EO, 20 EO, 25 EO, 30 EO or 40 EO.

The nonionic surfactants also include alkylglycosides of the formula $RO(G)_x$, in which R is a primary straight-chain or methyl-branched, in particular methyl-branched in the 2 position, aliphatic radical having 8 to 22, preferably 12 to 18, carbon atoms and 6 is a glycoside unit with 5 or 6 carbon atoms, preferably glucose. The degree of oligomerization x, which indicates the distribution of monoglycosides and oligoglycosides is any desired number—which, being a parameter to be determined analytically may also assume fractional values—between 1 and 10; preferably x is 1.2 to 1.4. Likewise suitable are polyhydroxy fatty acid amides of the formula (I) in which radical $R^1CO$ is an aliphatic acyl radical having 6 to 22 carbon atoms, $R^2$ is hydrogen; an alkyl or hydroxyalkyl radical having 1 to 4 carbon atoms and [Z] is a linear or branched polyhydroxylalkyl radical having 3 to 10 carbon atoms and 3 to 10 hydroxyl groups.

Preferably, the polyhydroxy fatty acid amides are derived from reducing sugars having 5 or 6 carbon atoms, in particular from glucose. The group of polyhydroxy fatty acid amides also includes compounds of the formula (II), $R^3$ is a linear or branched alkyl or alkenyl radical having 7 to 12 carbon atoms, $R^4$ is a linear, branched or cyclic alkylene radical or an arylene radical having 2 to 8 carbon atoms and $R^5$ is a linear, branched or cyclic alkyl radical or an aryl radical or an oxyalkyl radical having 1 to 8 carbon atoms, where $C_1$–$C_4$-alkyl or phenyl radicals are preferred, and [Z] is a linear polyhydroxyalkyl radical whose alkyl chain is substituted by at least two hydroxyl groups, or alkoxylated, preferably ethoxylated or propoxylated, derivatives of this radical. [Z] is here too preferably obtained by reductive amination of a sugar, such as glucose, fructose, maltose, lactose, galactose, mannose or xylose. The N-alkoxy or N-alyloxy-substituted compounds can then be converted into the desired polyhydroxy fatty acid amides by reaction of fatty acid methyl esters in the presence of an alkoxide as catalyst.

A further class of nonionic surfactants which is preferably used, which are used either as the sole nonionic surfactant or in combination with other nonionic surfactants, in particular together with alkoxylated fatty alcohols and/or alkylglycosides, are alkoxylated, preferably ethoxylated or ethoxylated and propoxylated, fatty acid alkyl esters, preferably having 1 to 4 carbon atoms in the alkyl chain, in particular fatty acid methyl esters. Nonionic surfactants of the amine oxide type, for example N-cocoalkyl-N,N-dimethylamine oxide and N-tallow-alkyl-N,N-dihydroxyethylamine oxide, and of the fatty acid alkanolamide type may also be suitable.

Suitable further surfactants are gemini surfactants. These are generally understood as meaning those compounds which have two hydrophilic groups per molecule. These groups are generally separated from one another by a spacer. This spacer is generally a carbon chain and should be long enough for the hydrophilic groups to have sufficient distance for them to be able to react independently of one another. Such surfactants are generally notable for an unusually low critical micelle concentration and the ability to greatly reduce the surface tension of water. However, it is also possible to use gemini polyhydroxy fatty acid amides or poly-polyhydroxy fatty acid amides. Further surfactant types may have dendrimeric structures.

Suitable organic and inorganic builders are salts which have a neutral or, in particular, alkaline reaction which are able to precipitate out or complex calcium ions. Suitable and particularly ecologically acceptable builder substances are crystalline, layered silicates of the formula $NaMSi_{(x)}O_{(2x+1)}$, where M is sodium or hydrogen, x is a number from 1.9 to 22, preferably from 1.9 to 4 and y is a number from 0 to 33, for example Na SKS-5 ($\alpha$-$Na_2Si_2O_5$), Na SKS-7 ($\alpha$-$Na_2Si_2O_5$, natrosilite), Na SKS-9 ($NaHSi_2O_5*H_2O$), Na SKS-10 ($NaHSi_2O_3*3H_2O$, canemite), Na SKS-11 (t-$Na_2Si_2O_5$) and Na SKS-13 ($NaHSi_2O_5$), but in particular Na SKS-6 ($\delta$-$Na_2Si_2O_5$), and also finely crystalline, synthetic hydrous zeolite, in particular of the NaA type which have a calcium-binding capacity in the range from 100 to 200 mg of CaO/g.

Zeolites and phyllosilicates may be present in the composition in an amount up to 20% by weight.

Also suitable are non-neutralized or partially neutralized (co)polymeric polycarboxylic acids. These include the homopolymers of acrylic acid or of methacrylic acid or copolymers thereof with further ethylenically unsaturated monomers, such as, for example, acrolein, dimethylacrylic acid, ethylacrylic acid, vinyl acetic acid, allyl acetic acid, maleic acid, fumaric acid, itaconic acid, meth(allylsulfonic acid), vinylsulfonic acid, styrenesulfonic acid, acrylamidomethylpropanesulfonic acid, and monomers containing phosphorus groups, such as, for example, vinylphosphoric acid, allylphosphoric acid and acrylamidomethylpropane-phosphoric acid and salts thereof, and hydroxyethyl (meth)acrylate sulfate, allyl alcohol sulfate and allyl alcohol phosphates.

Preferred (co)polymers have an average molar mass of from 1000 to 100 000 g/mol, preferably from 2000 to 75 000 g/mol and in particular from 2000 to 35 000 g/mol.

The degree of neutralization of the acid groups is advantageously 0 to 90%, preferably 10 to 80% and in particular 30 to 70%.

Suitable polymers include in particular also homopolymers of acrylic acid and copolymers of (meth)acrylic acid with maleic acid or maleic anhydride.

Further suitable copolymers are derived from terpolymers, which can be obtained by polymerization of 10 to 70% by weight of monoethylenically unsaturated dicarboxylic acids having 4 to 8 carbon atoms, salts thereof, 20 to 85% by weight of monoethylenically unsaturated monocarboxylic acids having 3 to 10 carbon atoms or salts thereof, 1 to 50% by weight of monounsaturated monomers which, following hydrolysis, release hydroxyl groups at the polymer chain, and 0 to 10% by weight of further, free-radically copolymerizable monomers.

Likewise suitable are graft polymers of monosaccharides, oligosaccharides, polysaccharides and modified polysaccharides, and animal or vegetable proteins.

Preference is given to copolymers of sugar and other polyhydroxy compounds and a monomer mixture of 45 to 96% by weight of monoethylenically unsaturated $C_3$–$C_{10}$-monocarboxylic acids or mixtures of $C_3$–$C_{10}$-monocarboxylic acids and/or salts thereof with monovalent cations, 4 to 55% by weight of monoethylenically unsaturated monomers containing monosulfonic acid groups, monoethylenically unsaturated sulfuric esters, vinylphosphoric esters and/or the salts of these acids with monovalent cations, and 0 to 30% by weight of water-soluble unsaturated compounds which have been modified with 2 to 50 mol of alkylene oxide per mole of monoethylenically unsaturated compounds.

Further suitable polymers are polyaspartic acid or derivatives thereof in nonneutralized or only partially neutralized form.

Graft polymers of acrylic acid, methacrylic acid, maleic acid and further ethylenically unsaturated monomers on salts of polyaspartic acid, as are usually produced during the above-described hydrolysis of polysuccinimide are particularly suitable. Here, it is possible to dispense with the otherwise necessary addition of acid for the preparation of the only partially neutralized form of polyaspartic acid. The amount of polyaspartate is usually chosen so that the degree of neutralization of all carboxyl groups incorporated within the polymer does not exceed 80%, preferably 60%.

Further builders which can be used are, for example, the percarboxylic acids preferably used in the form of their sodium salts, such as citric acid, in particular trisodium citrate and trisodium citrate dihydrate, nitrilotriacetic acid and its water-soluble salts; the alkali metal salts of carboxymethyloxysuccinic acid, ethylenediaminetetraacetic acid, mono-, dihydroxysuccinic acid, α-hydroxypropionic acid, gluconic acid, mellitic acid, benzopolycarboxylic acids and those as disclosed in U.S. Pat. Nos. 4,144,226 and 4,146,495.

Phosphate-containing builders, for example alkali metal phosphates, which may be present in the form of their alkaline, neutral or acidic sodium or potassium salts, are also suitable.

Examples thereof are trisodium phosphate, tetrasodium diphosphate, disodium dihydrogenphosphate, pentasodium triphosphate, so-called sodium hexametaphosphate, oligomeric trisodium phosphate with oligomerization amounts in the range from 5 to 1000, in particular 5 to 50, and mixtures of sodium and potassium salts.

These builder substances may be present from 5 to 80% by weight, a content of from 10 to 60% by weight is preferred.

The desired viscosity of the liquid compositions can be adjusted by adding water and/or organic solvents or by adding a combination of organic solvents and thickeners.

In principle, suitable organic solvents are all mono- or polyhydric alcohols. Preference is given to using alcohols having 1 to 4 carbon atoms, such as methanol, ethanol, propanol, isopropanol, straight-chain and branched butanol, glycerol and mixtures of said alcohols. Further preferred alcohols are polyethylene glycols with a relative molecular mass below 2000. In particular, a use of polyethylene glycol with a relative molecular mass between 200 and 600 and in amounts up to 45% by weight and of polyethylene glycol with a relative molecular mass between 400 and 600 in amounts of from 5 to 25% by weight is preferred. An advantageous mixture of solvents consists of monomeric alcohol, for example ethanol and polyethylene glycol in the ratio 0.5:1 to 1.2:1.

Further suitable solvents are, for example, triacetin (glycerol triacetate) and 1-methoxy-2-propanol.

The thickeners used are preferably hydrogenated castor oil, salts of long-chain fatty acids, which preferably in amounts of from 0 to 5% by weight and in particular in amounts of from 0.5 to 2% by weight, for example sodium, potassium, aluminum, magnesium and titanium stearates or the sodium and/or potassium salts of behenic acid, and polysaccharides, in particular xanthan gum, guar guar, agar agar, alginates and Tyloses, carboxymethylcellulose and hydroxyethylcellulose, and also higher molecular weight polyethylene glycol mono- and diesters of fatty acids, polyacrylates, polyvinyl alcohol and polyvinylpyrrolidone, and electrolytes such as sodium chloride and ammonium chloride.

Suitable thickeners are water-soluble polyacrylates, which are crosslinked, for example, with about 1% of a polyallyl ether of sucrose and which have a relative molecular mass above one million. Examples thereof are the polymers obtainable under the name Carbopol® 940 and 941. The crosslinked polyacrylates are used in amounts not exceeding 1% by weight, preferably in amounts of from 0.2 to 0.7% by weight.

The enzymes optionally present in compositions according to the invention include proteases, amylases, pullulanases, cellulases, cutinases and/or lipases, for example proteases, such as BLAP®, Optimase®, Opticlean®, Maxacal®, Maxapem®, Durazym®, Purafect® OxP, Esperase® and/or Savinase®, amylases, such as Termamy®, Amylase-LT, Maxamyl®, Duramyl®, Purafectel OxAm, cellulases, such as Celluzyme®, Carezyme®, K-AC® and/or the cellulases known from the international patent applications WO 96/34108 and WO 96/34092 and/or lipases, such as Lipolase®, Lipomax®, Lumafast® and/or Lipozym®. The enzymes used can, as described, for example, in international patent applications WO 92/111347 or WO 94/23005, be absorbed to carrier substances and/or be embedded in coating substances in order to protect them from premature deactivation. They are present in washing and cleaning compositions according to the invention preferably in amounts up to 10% by weight, in particular from 0.05 to 5% by weight, particular preference being given to using enzymes stabilized against oxidative degradation.

Preferably, machine dishwashing detergents according to the invention comprise the customary alkali carriers, such as, for example, alkali metal silicates, alkali metal carbonates and/or alkali metal hydrogen carbonates. The customarily used alkali carriers include carbonates, hydrogen carbonates and alkali metal silicates with an $SiO_2/M_2O$ (M=alkali metal atom) molar ratio of from 1:1 to 2.5:1. Alkali metal silicates may be present here in amounts of up to 40% by weight, in particular 3 to 30% by weight, based on the total composition. The alkali carrier system preferably used in cleaning compositions according to the invention is a mixture of carbonate and hydrogen carbonate, preferably sodium carbonate and hydrogen carbonate, which may be present in an amount of up to 50% by weight, preferably 5 to 40% by weight.

The invention further provides for a composition for machine dishwashing, comprising 15 to 65% by weight, in particular 20 to 60% by weight, of water-soluble builder component, 5 to 25% by weight, in particular 8 to 17% by weight, of oxygen-based bleaching agent, in each case based on the total composition, and 0.1 to 5% by weight of one or more of the cationic nitrilic activators defined above. Such a composition is preferably low-alkaline, i.e. its percentage by weight solution has a pH of from 8 to 11.5, in particular 9 to 11.

In a further embodiment of compositions according to the invention for automatic dishwashing, 20 to 60% by weight of water-soluble organic builders, in particular alkali metal citrate, 3 to 20% by weight of alkali metal carbonate and 3 to 40% by weight of alkali metal disilicate are present.

In order to effect silver corrosion protection, silver corrosion inhibitors may be used in dishwashing compositions according to the invention. Preferred silver corrosion protectants are organic sulfides, such as cystine and cysteine, di- or trihydric phenols, optionally alkyl- or aryl-substituted triazoles, such as benzotriazole, isocyanuric acid, and salts and/or complexes of titanium, zirconium, hafnium, molybdenum, vanadium or cerium.

If the compositions foam too much upon use, up to 6% by weight, preferably about 0.5 to 4% by weight, of a foam-regulating compound, preferably from the group comprising silicones, paraffins, paraffin/alcohol combinations, hydrophobicized silicas, bis fatty acid amides and mixtures thereof and other known commercially available foam inhibitors may also be added to them. The foam inhibitors, in particular silicone- and/or paraffin-containing foam inhibitors, are preferably bonded to a granular, water-soluble or -dispersible carrier substance. In particular, mixtures of paraffins and bistreaylethylenediamide are preferred. Further optional ingredients in the compositions according to the invention are, for example, perfume oils.

Organic solvents which can be used in the compositions according to the invention, particularly when they are in liquid or paste form, include alcohols having 1 to 4 carbon atoms, in particular methanol, ethanol, isopropanol and tert-butanol, diols having 2 to 4 carbon atoms, in particular ethylene glycol and propylene glycol, and mixtures thereof and the ethers which can be derived from said classes of compound. Such water-miscible solvents are present in the cleaning compositions according to the invention preferably not exceeding 20% by weight, in particular from 1 to 15% by weight.

To establish a desired pH which does not arise by itself as a result of mixing the other components, the compositions according to the invention may comprise system-compatible and environmentally compatible acids, in particular citric acid, acetic acid, tartaric acid, malic acid, lactic acid, glycolic acid, succinic acid, glutaric acid and/or adipic acid, but also mineral acids, in particular sulfuric acid or alkali metal hydrogensulfates, or bases, in particular ammonium or alkali metal hydroxides. Such pH regulators are present in the compositions according to the invention preferably not exceeding 10% by weight, in particular from 0.5 to 6% by weight.

Suitable preservatives are, for example, phenoxyethanol, formaldehyde solution, pentanediol or sorbic acid.

Suitable perlizing agents are, for example, glycol distearic esters, such as ethylene glycol distearate, but also fatty acid monoglycol esters. Suitable salts or extenders are, for example, sodium sulfate, sodium carbonate or sodium silicate (waterglass).

Typical individual examples of further additives are sodium borate, starch, sucrose, polydextrose, RAED, stilbene compounds, methylcellulose, toluenesulfonate, cumenesulfonate, soaps and silicones.

The compositions according to the invention are preferably in the form of pulverulent, granular or tablet-shaped preparations which can be produced in a manner known per se, for example by mixing, granulation, roll compaction and/or by spray-drying the thermally stable components and mixing in the more sensitive components, which include in particular enzymes, bleaching agents and the bleaching catalyst. Compositions according to the invention in the form of aqueous solutions or solutions comprising other customary solvents are particularly advantageously prepared by simple mixing of the ingredients, which can be added without a diluent or in the form of a solution to an automatic mixer.

To prepare particulate compositions with increased bulk density, in particular in the range from 650 g/l to 950 g/l, a process having an extrusion step and known from European patent specification EP 0 486 592 is preferred. A further preferred preparation using a granulation process is described in European patent specification EP 0 642 576. The preparation of compositions according to the invention in the form of non-dusting, storage-stable, flowable powders and/or granules with high bulk densities in the range from 800 to 1000 g/l can also be carried out by, in a first process stage, mixing the builder components with at least a proportion of liquid mixing components to increase the bulk density of this premix and subsequently—if desired after intermediate drying—combining the further constituents of the composition, including the cationic, nitrilic activator, with the premix obtained in this way.

Compositions according to the invention in tablet form are preferably prepared by mixing all of the constituents together in a mixer and compressing the mixture by means of conventional tablet presses, for example eccentric presses or rotary presses. This gives, without problems, tablets which are fracture-resistant but nevertheless sufficiently rapidly soluble under application conditions, and have flexural strength of normally more than 150 N. A tablet produced in this way preferably has a weight of 1–5 g to 40 g, in particular from 20 g to 30 g; with a diameter of 3–5 mm to 40 mm.

In addition to the ingredients already mentioned, the washing and cleaning compositions can comprise any of the conventional additives in amounts which are usually found in such compositions.

EXAMPLES

Example 1

Synthesis of (cyanomethyl)-di-n-hexylmethylammonium Chloride 10 g (0.05 mol) of dihexylmethylamine were initially introduced into 50 ml of acetone at room temperature. Over the course of 10 minutes, 3.8 g (0.05 mol) of chloroacetonitrile were added dropwise and the mixture was stirred for about 8 hours at 50° C. After this time, TLC monitoring reveals no more starting material. The mixture was concentrated completely by evaporation and the residue was washed three times with diethyl ether. The combined ethereal phases were freed completely from the solvent on a rotary evaporator. This gave 12.7 g (0.046 mol) of (cyanomethyl)-di-n-hexylmethylammonium chloride as a yellow, viscose oil, corresponding to a yield of 92%.

Example 2

Synthesis of di-n-hexylaminoacetonitrile 95.6 g (0.5 mol) of di-n-hexylamine were dissolved in 200 ml of absolute ethanol and admixed with 26.5 g (0.25 mol) of sodium carbonate. At room temperature, 37.8 g (0.5 mol) of chloroacetonitrile were added dropwise over the course of 30 min. Stirring was then carried out for 16 hours at 60° C. and the reaction mixture was poured onto 800 ml of water. Following phase separation, the organic phase was washed with 3×50 ml of water, taken up in methylene chloride, dried over magnesium sulfate, filtered and concentrated by evaporation. This gave a pale brown liquid which is purified by fractional distillation. The fractions between 104 and 111° C. at 25 mbar were collected. This gave 95.6 g (0.43 mol) of pure di-n-hexylaminoacetonitrile, corresponding to a yield of 86%.

Example 3

Synthesis of (cyanomethyl)-di-n-hexylmethylammonium Methosulfate 11.2 g (0.05 mol) of di-n-hexylaminoacetonitrile were initially introduced into 50 ml of acetonitrile. 6.3 g (0.05 mol) of dimethyl sulfate were added dropwise over the course of 5 minutes and the mixture was stirred for about 120 hours at room temperature. The clear solution was concentrated by evaporation on a rotary evaporator and the residue was recrystallized from diethyl ether. After the crystal slurry had been filtered off with suction, it was then washed with diethyl ether and dried in a vacuum drying cabinet. This gave 16.8 g (0.048 mol) of (cyanomethyl)-di-n-hexylmethylammonium methosulfate as a white crystalline solid, corresponding to a yield of 96%.

Example 4

Synthesis of (cyanomethyl)-di-n-hexylmethylammonium Benzenesulfonate 18.0 g (0.08 mol) of dihexylaminoacetonitrile were initially introduced into 50 ml of ethyl acetate. 13.8 g (0.08 mol) of methyl benzenesulfonate were added dropwise to this solution at room temperature over the course of 10 min. The mixture was stirred for 24 hours at room temperature, and the clear solution was concentrated by evaporation on a rotary evaporator. The residue was stirred out with diethyl ether and the precipitated solid was filtered off with suction. It was washed with diethyl ether and then dried at 50° C. in a vacuum drying cabinet. This gave 20.5 g (0.052 mol) of (cyanomethyl)-di-n-methylammonium benzenesulfonate of a white powder, corresponding to a yield of 65%.

Example 5

Synthesis of di-n-octylaminoacetonitrile 73.9 g (0.3 mol) of di-n-octylamine were initially introduced together with 31.8 g (0.3 mol) of sodium carbonate into 240 ml of absolute ethanol. At room temperature, 22.9 g (0.3 mol) of chloroacetonitrile were added and the mixture was stirred at reflux until starting material could no longer be detected by means of thin-layer chromatography (stationary phase: silica gel; mobile phase: methanol). The reaction mixture was filtered off and the filtrate was evaporated to dryness on a rotary evaporator. The residue was subjected to fractional distillation. At 145° C. and 0.04 mbar a fraction is obtained which is pure according to NMR spectroscopy. 58.4 g (0.21 mol) of di-n-octylaminoacetonitrile were isolated in the form of a clear liquid, corresponding to a yield of 69%.

Example 6

Synthesis of (cyanomethyl)-di-n-octylmethylammonium Toluenesulfonate 28.1 g (0.1 mol) of di-n-octylaminoacetonitrile were stirred together with 18.6 g (0.1 mol) of methyl toluenesulfonate in 100 ml of ethyl acetate for 16 hours at 60° C. The clear solution was concentrated on a rotary evaporator and the residue was stirred out in diethyl ether. The resulting solid was filtered off with suction, washed with diethyl ether and dried under reduced pressure. This gave 15.7 g (0.034 mol) of (cyanomethyl)-di-n-octylmethylammonium toluenesulfonate as a white solid, corresponding to a yield of 34%.

Example 7

Synthesis of Methyl Cumenesulfonate 594.9 g (5.0 mol) of thionyl chloride were initially introduced together with 1 g of DMF, and 222.2 g (1.0 mol) of sodium cumenesulfonate were slowly added in portions starting at room temperature. The mixture was stirred at reflux for 16 hours and 250 ml of chloroform were added after cooling. Following filtration, excess thionyl chloride was stripped off together with the chloroform under reduced pressure. 250 ml of methanol were added, and a pH of 7.0 was established using 25% strength sodium hydroxide solution at 25° C. The mixture was then stirred out with dichloromethane, the organic phase was concentrated on a rotary evaporator, and the residue obtained was subjected to fractional distillation under reduced pressure. At 102° C. and 0.03 mbar, 96.9 g (0.44 mol) of methyl cumenesulfonate were isolated in the form of a clear liquid, corresponding to a yield of 44%.

Example 8

Synthesis of (cyanomethyl)-di-n-octylmethylammonium Cumenesulfonate 28.1 g (0.1 mol) of di-n-octylaminoacetonitrile were initially introduced into 100 ml of ethyl acetate and, following the addition of 21.4 g (0.1 mol) of methyl cumenesulfonate, were stirred at reflux for 16 hours. The solid obtained was filtered off with suction, washed with diethyl ether and dried under reduced pressure. This gave 20.0 g (0.04 mol) of (cyanomethyl)-di-n-octylmethylammonium cumenesulfonate in the form of a white solid, corresponding to a yield of 40%.

Example 9

The cationic nitrile compounds according to the invention were used to prepare bleaching composition formulations, with which washing experiments on a hydrophobic soiling (curry) were carried out. The basis of the bleaching composition formulations was an aqueous solution of a phosphate-free base detergent (reference detergent WMP from WFK-Testgewebe GmbH Krefeld) with a concentration of 2 g/l of WMP in water of 15° German hardness. For this 0.5 g/l of sodium perborate monohydrate and varying amounts of the cationic nitrile compounds were weighed in.

Using these formulations, bleaching-sensitive standard test fabric from Wätschereiforschung Krefeld (WFK) with the soiling of curry (BC-4) were subjected, in a Linitest apparatus (Heraeus), to a treatment at a temperature of 20 or 40° C. under isothermal washing conditions. After a washing time of 30 minutes, the fabric sections were rinsed with water, dried and ironed. The bleaching effect was then quantified by determining the difference ΔR (formulation+activator) of the reflectances before and after the washing operation using a device for measuring degree of whiteness (ELREPHO 2000, Datacolor). These ΔR (formulation+activator) values and the values ΔR (formulation) determined in controlled experiments without cationic nitrile compound were used to calculate the ΔΔR values listed in the tables below, which represent a direct measure of the improvement in the bleaching effect brought about by the addition of cationic nitrile compound:

ΔΔR=ΔR(formulation+activator)−ΔR(formulation)

Bleaching compositions containing the cationic nitrile compounds 3 to 7 according to the invention, and also the comparison substances 1 and 2 were prepared.

The compounds 1 to 7 are

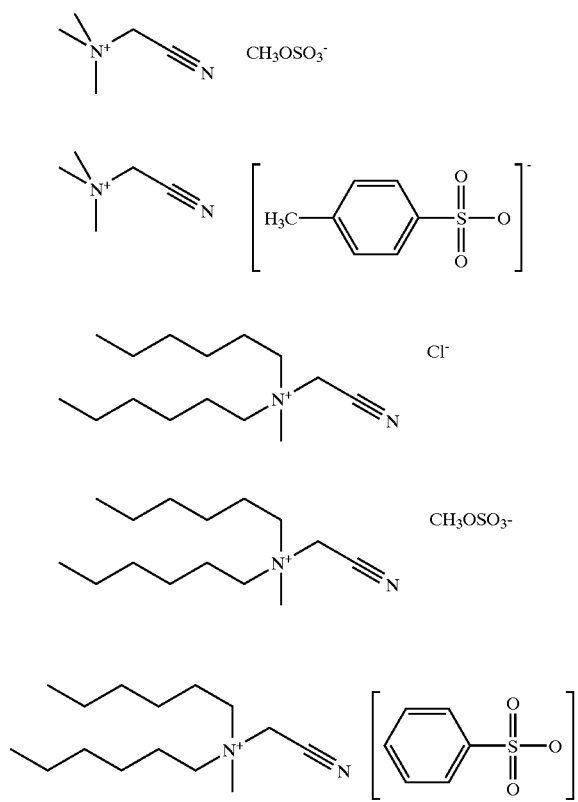

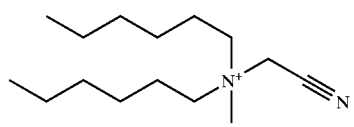

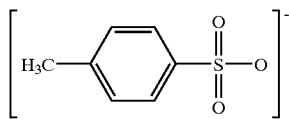

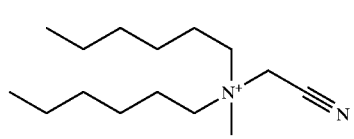

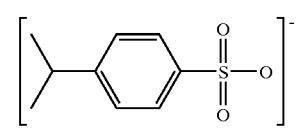

With activators 3 and 4, washing experiments were carried out at 20 and 40° C., at concentrations of 0.3 or 0.5 g/l. The results are compared in Table 1 with activator 1:

TABLE 1

Test results (ΔΔR values) for activators 3 and 4

| Washing conditions | Activator 3 | Activator 4 | Activator 1 |
| --- | --- | --- | --- |
| 20° C.; c(activator) = 0.3 g/l | 4.1 | 2.3 | 1.8 |
| 20° C.; c(activator) = 0.5 g/l | 4.0 | 3.5 | 2.0 |
| 40° C.; c(activator) = 0.3 g/l | 5.0 | 4.7 | 4.2 |
| 40° C.; c(activator) = 0.5 g/l | 7.3 | 5.6 | 4.1 |

For activators 5 to 7, washing experiments were carried out at 20 and 40° C. at a concentration of 0.25 g/l. The results are compared in Table 2 with activator 2 and also with TAED:

TABLE 2

Test results (ΔΔr values) for activators 5 to 7: c(activator) = 0.25 g/l

| Washing conditions | Activator 5 | Activator 6 | Activator 7 | Activator 2 | TAED |
| --- | --- | --- | --- | --- | --- |
| 20° C. | 2.9 | 2.8 | 4.1 | 2.6 | 0.1 |
| 40° C. | 4.6 | 4.6 | 5.6 | 3.1 | 1.3 |

The experiments show that the cationic nitrites according to the invention develop a better bleaching effect on hydrophobic soilings than the cationic activators of the prior art or than TAED. Further useful properties of the cationic nitrites are low color damage and low fiber damage.

The invention claimed is:
1. A washing, cleaning or disinfecting composition comprising a surfactant and a compound of the formula (I)

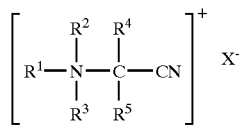

in which $R^1$ and $R^2$ are in each case individually a straight-chain or branched-chain,
$R^3$ is methyl,
$R^4$ and $R^5$ are hydrogen, $C_1$–$C_4$-alkyl, $C_2$–$C_4$-alkenyl, $C_1$–$C_4$-alkoxy-$C_1$–$C_4$-alkyl, phenyl, $C_1$- to $C_3$-alkylphenyl or together with the common carbon atom form a $C_5$–$C_7$-cycloalkyl group, $R_4$ is hydrogen if $R_5$ is not hydrogen, and
$X^-$ is an anion.

2. A composition as claimed in claim 1, wherein $R^1$ and $R^2$ are in each case individually a $C_5$–$C_{18}$-alkyl, alkenyl or alkyl ether group.

3. A composition as claimed in claim 1, wherein $R^4$ and $R^5$ are hydrogen.

4. A composition as claimed in claim 1, wherein $X^-$ is chloride, bromide, iodide, fluoride, sulfate, hydrogensulfate, carbonate, hydrogencarbonate, phosphate, mono- and dihydrogenphosphate, pyrophosphate, metaphosphate, nitrate, methosulfate, dodecylsulfate, dodecylbenzenesulfonate, phosphonate, methylphosphonate, methanedisulfonate, methylsulfonate, ethanesulfonate, toluenesulfonate, benzenesulfonate or cumenesulfonate.

5. A composition as claimed in claim 1, wherein $R^1$ and $R^2$ is $C_6$–$C_{10}$-alkyl, $R^3$ is methyl, $R^4$ and $R^5$ are hydrogen and $X^-$ is an anion.

6. A composition as claimed in claim 1, wherein $R^1$ and $R^2$ is $C_6$–$C_{10}$-alkyl, $R^3$ is methyl, $R^4$ and $R^5$ are hydrogen and $X^-$ is chloride, hydrogensulfate, sulfate, methosulfate, toluenesulfonate, benzenesulfonate or cumenesulfonate.

7. A bleaching composition for the bleaching of textile material and paper comprising a peroxygen bleach and a compound of the formula (I)

in which $R^1$ and $R^2$ are in each case individually a straight-chain or branched-chain $C_5$–$C_{24}$ alkyl, $R^3$ is methyl, $R^4$ and $R^5$ are hydrogen, $C_1$–$C_4$-alkyl, $C_2$–$C_4$-alkenyl, $C_1$–$C_4$-alkoxy-$C_1$–$C_4$-alkyl, $C_1$- to $C_3$-alkylphenyl or together with the common carbon atom form a $C_5$–$C_7$-cycloalkyl group, $R^4$ is hydrogen if $R^5$ is not hydrogen, and $X^-$ is an anion.

* * * * *